(12) United States Patent
Choi

(10) Patent No.: US 6,394,810 B1
(45) Date of Patent: May 28, 2002

(54) DENTAL PROSTHESIS

(76) Inventor: Ki Sun Choi, 303-304 Mirastown Apt. Samsanjugong 390-6 Samsan-dong Bupyung-gu, Inchon (KR)

(*) Notice: Subject to any disclaimer, the term of this patent is extended or adjusted under 35 U.S.C. 154(b) by 0 days.

(21) Appl. No.: 09/708,629

(22) Filed: Nov. 9, 2000

(30) Foreign Application Priority Data

Nov. 9, 1999 (KR) .......................................... 99-024381

(51) Int. Cl.[7] .............................................. A61C 13/225
(52) U.S. Cl. ....................................... 433/180; 433/181
(58) Field of Search ................................ 433/180, 181, 433/182, 183, 177, 178

(56) References Cited

U.S. PATENT DOCUMENTS

| | | | | |
|---|---|---|---|---|
| 2,266,285 A | * | 12/1941 | Stern | 433/177 |
| 3,818,594 A | * | 6/1974 | Gil-Castillo | 433/177 |
| 4,475,891 A | * | 10/1984 | Hader | 433/181 |
| 4,583,948 A | * | 4/1986 | Jansen | 433/181 |
| RE32,972 E | * | 7/1989 | Harvey, Sr. et al. | 433/181 |

* cited by examiner

Primary Examiner—Nicholas D. Lucchesi
Assistant Examiner—Melba Bumgarner
(74) Attorney, Agent, or Firm—Jacobson Holman, PLLC

(57) ABSTRACT

Disclosed is a dental prosthesis. The dental prosthesis comprises an artificial tooth replacing a decayed tooth, the artificial tooth being made of a suitable material such as metal or ceramic and being arranged between two adjoining teeth which are respectively located at both sides of the decayed tooth, so as to take the place of the decayed tooth; and a pair of securing means for securing the artificial tooth to the two adjoining teeth, the artificial tooth serving as a female coupling element and each securing means serving as a male coupling element, whereby a prosthetic dentistry can be independently implemented,

11 Claims, 6 Drawing Sheets

DENTAL PROSTHESIS

BACKGROUND OF THE INVENTION

1. Field of the Invention

The present invention relates to a dental prosthesis, and more particularly, the present invention relates to a dental prosthesis which is configured to secure an artificial tooth made of metal, ceramic or the like, in a manner such that the artificial tooth takes the place of an extracted tooth.

2. Description of the Related Art

Generally, an individual normally has thirty-two teeth as a whole, including an upper set of sixteen teeth and a lower set of sixteen teeth. As a child grows, all deciduous teeth which are completed in babyhood, are replaced with permanent teeth, and using these permanent teeth, mastication is executed throughout one's whole life.

After the permanent teeth are formed as described above, one or more teeth can be decayed due to a diversity of dental diseases, such as a decay, a gumboil or the like. In this case, because sufficient stability is not provided under all pronouncing or chewing conditions and an aesthetic appearance is deteriorated, there are frequent occasions where a normal social life is adversely affected by the decayed teeth.

In an attempt to replace a decayed tooth, a dental prosthesis is employed, so that a masticating function, an aesthetic appearance and a normal pronunciation are recovered.

Dental prostheses are divided into a general dental prosthesis which replaces a severely decayed tooth, covers a decayed tooth or a tooth weakened by a nervous treatment or the like or fills a vanished portion of a tooth, an aesthetic prosthesis which repairs discolored teeth mainly in an anterior set of teeth and abnormally shaped teeth or removes a crevice defined between two teeth, and a fixed dental implant prosthesis which is installed by implanting an artificial tooth root element at a place where a decayed tooth is extracted and by securing an artificial tooth to the tooth root element, in such a way as to avoid inconvenience which can be induced upon grinding adjoining healthy teeth and using the artificial tooth in the general dental prosthesis.

Among the dental prostheses which are divided as described above, the general dental prosthesis which functions to replace a decayed tooth with an artificial tooth, is used, as can be readily seen from FIGS. 1 and 2, in a manner such that a pair of cap segments 11 which respectively define inner spaces corresponding to contours of two adjoining teeth 10, are integrally connected to an artificial tooth 12 so as to fixedly maintain the artificial tooth 12 and the entire dental prosthesis is fitted on the two adjoining teeth 10.

Since the dental prosthesis which is fitted on the two adjoining teeth 12, has a-shape which is similar to that of a crown, the general dental prosthesis is called a crown bridge 1.

While the crown bridge 1 provides advantages in that the prosthetic dentistry is simplified and the cost is reduced, due to the fact that the two adjoining teeth 10 which are respectively located at both sides of the artificial tooth 12, must be ground down by a thickness corresponding to the pair of cap segments 11 used for fixedly maintaining the artificial tooth 12, the two adjoining teeth 10 which are normally healthy, can be damaged. Also, if air, foreign substances and so forth flow into gaps which are defined between the two adjoining teeth 10 and the pair of cap segments 11, a serious problem can be induced in that the healthy teeth can begin to decay.

In this regard, the fixed dental implant prosthesis is provided to cope with disadvantages occurring in the general dental prosthesis. As described above, the fixed dental implant prosthesis is installed by implanting the artificial tooth root element into an upper jaw or a lower jaw at the place where the decayed tooth is extracted and by securing the artificial tooth to the artificial tooth root element using screws. In this way, unlike the case of the general dental prosthesis, the two adjoining healthy teeth are not degraded in their quality, and ill effects which can result from implementing a prosthetic dentistry device can be avoided.

However, the fixed dental implant prosthesis still suffers from defects in that a period of from six months to a year is often required for completing the prosthetic dentistry. and the cost is very high.

Moreover, implanting the artificial tooth root element, which is made of metal, into th e upper or lower jaw can cause mental trauma to the dentistry receiver, reducing the effectiveness of the prosthetic dentistry. Further, because the artificial tooth which is secured using the fixed dental implant prosthesis has reduced side-impact resistance, when a load is applied to the artificial tooth, the likelihood of serious damage to the upper and lower jaws is increased.

However, the fixed dental implant prosthesis still suffers from defects in that a period of six months at the least or one year at the most is required for completing the prosthetic dentistry, and a huge amount of cost is needed.

Moreover, by the fact that the artificial tooth root element which is made of metal, is implanted into the upper or lower jaw, since a mental burden is imposed on a dentistry receiver, an effectiveness of the prosthetic dentistry is impaired. Further, because the artificial tooth which is secured using the fixed dental implant prosthesis, has reduced is side-impact resistance, when a load is applied to the artificial tooth, the likelihood of the upper and lower jaws to be seriously damaged, is increased.

SUMMARY OF THE INVENTION

Accordingly, the present invention has been made in an effort to solve the problems occurring in the related art, and an object of the present invention is to provide a dental prosthesis which replaces a decayed tooth in a manner such that an artificial tooth can be independently secured to two adjoining teeth without using an artificial tooth root element and the two adjoining teeth and upper and lower jaws are prevented from being damaged, and to this end, includes an artificial tooth and a pair of securing means for securing the artificial tooth to two adjoining teeth, in a manner such that the artificial tooth serves as a female coupling element and each securing means serves as a male coupling element, whereby a prosthetic dentistry is simplified and a required sum is reduced, and a human-friendly prosthetics is enabled.

In order to achieve the above object, according to one aspect of the present invention, there is provided a dental prosthesis comprising: an artificial tooth replacing a decayed tooth, the artificial tooth being made of a suitable material such as metal or ceramic and being arranged between two adjoining teeth which are respectively located at both sides of the decayed tooth, so as to take the place of the decayed tooth; and a pair of securing means for securing the artificial tooth to the two adjoining teeth, the artificial tooth serving as a female coupling element and each securing means serving as a male coupling element, whereby a prosthetic dentistry can be independently implemented.

According to another aspect of the present invention, the artificial tooth made of metal or ceramic, which constitutes the dental prosthesis and is independently secured, is defined, at both side walls thereof, with a pair of fitting grooves, respectively, which are opened at lower ends of the side walls and extend upward to a point corresponding to about ⅔ of a height of the artificial tooth in consideration of pressure resistance; the pair of securing means comprise a pair of inlay members which are respectively mounted to opposite side surfaces of the two adjoining teeth, so as to secure the artificial tooth to the two adjoining teeth; and each inlay member has substantially an H-shaped cross-section and comprises a fitting part which is fitted into the fitting groove defined in the side wall of the artificial tooth and a securing part which is formed with a plurality of projections in a manner such that the projections obliquely extend downward to define a predetermined angle with respect to a horizontal line and the securing part is secured by the medium of the projections to the two adjoining teeth.

According to still another aspect of the present invention, each adjoining tooth to which the securing part of each inlay member constituting the securing means of the dental prosthesis is secured, is defined with a plurality of inserting grooves in which the plurality of projections are respectively inserted, the inserting grooves obliquely extending downward to define the predetermined angle with respect to the horizontal line.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Figure 1:
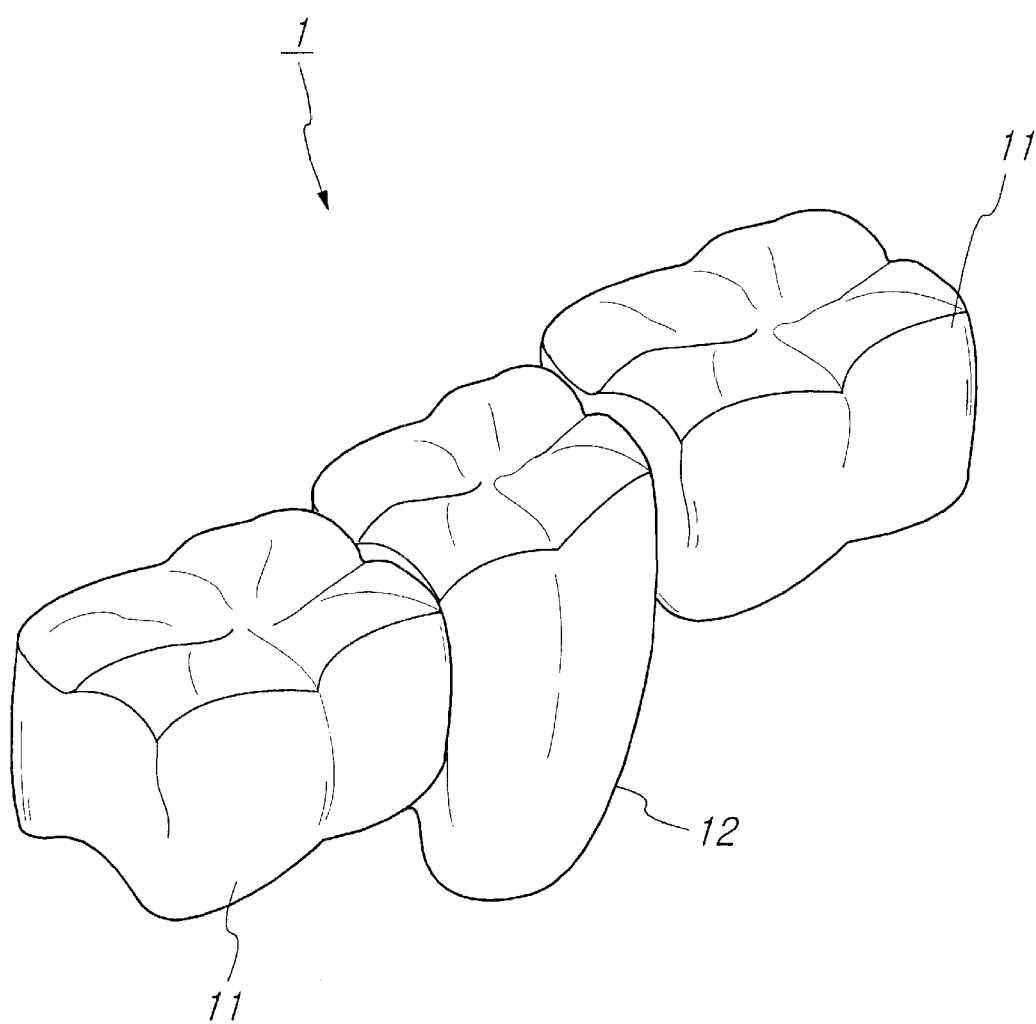
FIG. 1 is a perspective view illustrating a conventional dental prosthesis.
Figure 2:
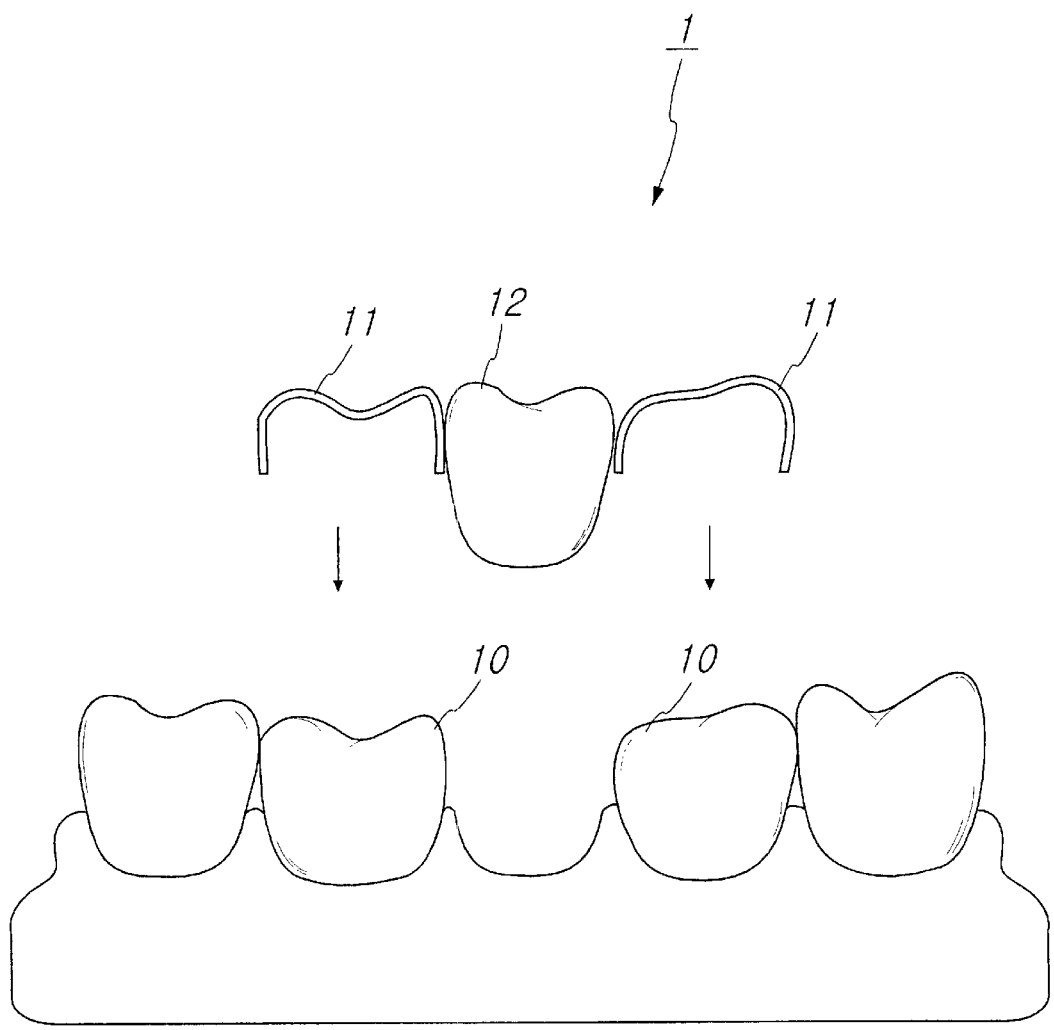
FIG. 2 is a cross-sectional view illustrating a state wherein the conventional dental prosthesis is about to be fitted between two adjoining teeth.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 3:
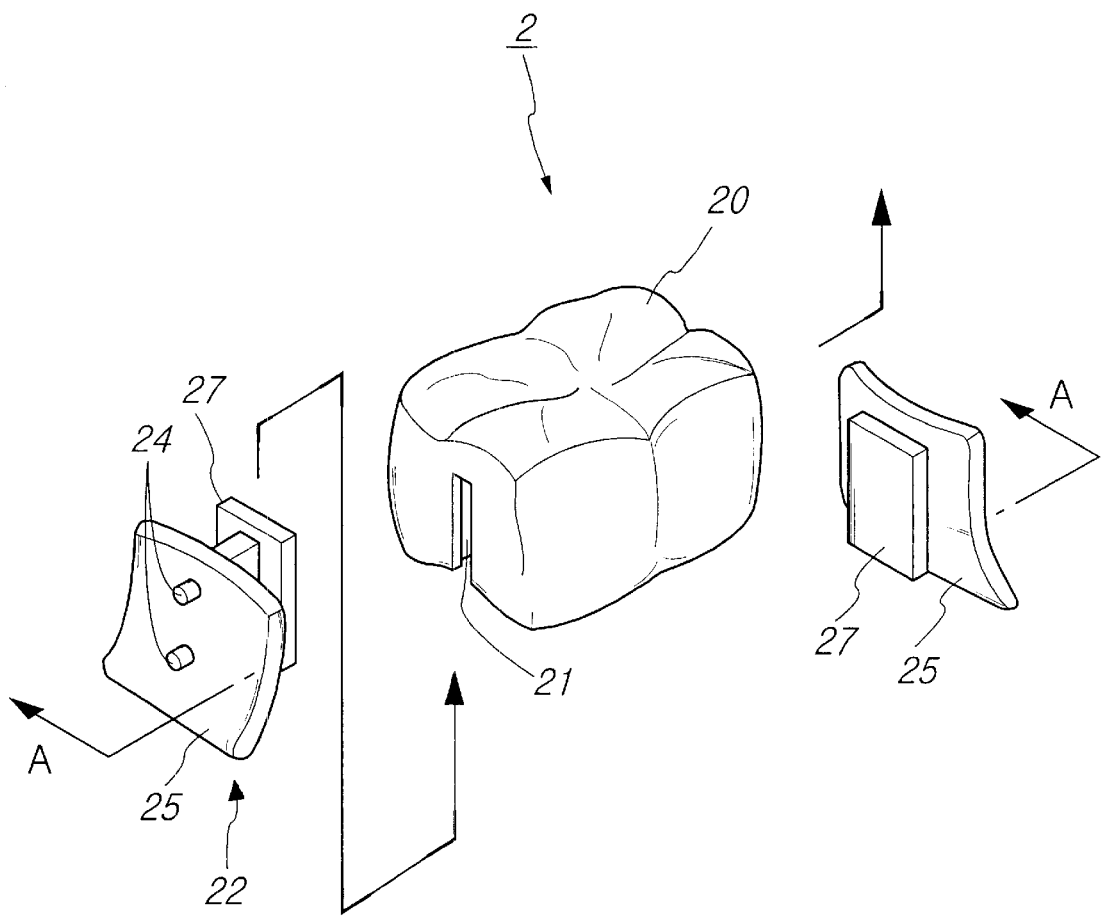
FIG. 3 is an exploded perspective view illustrating an entire construction of a dental prosthesis in accordance with an embodiment of the present invention.
Figure 4:
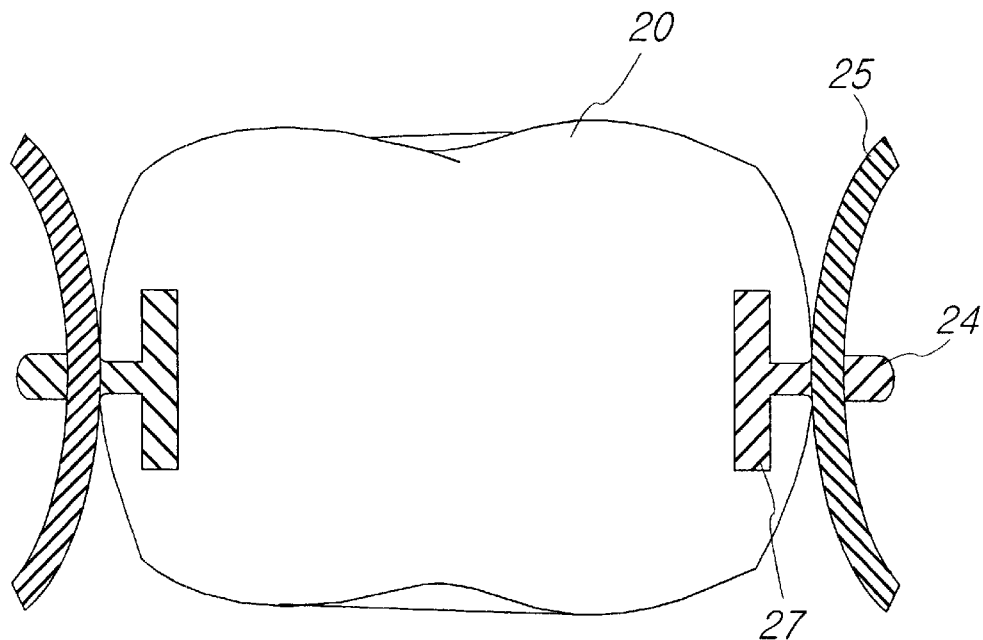
FIG. 4 is a cross-sectional view taken along the line A—A of FIG. 3.
Figure 5:
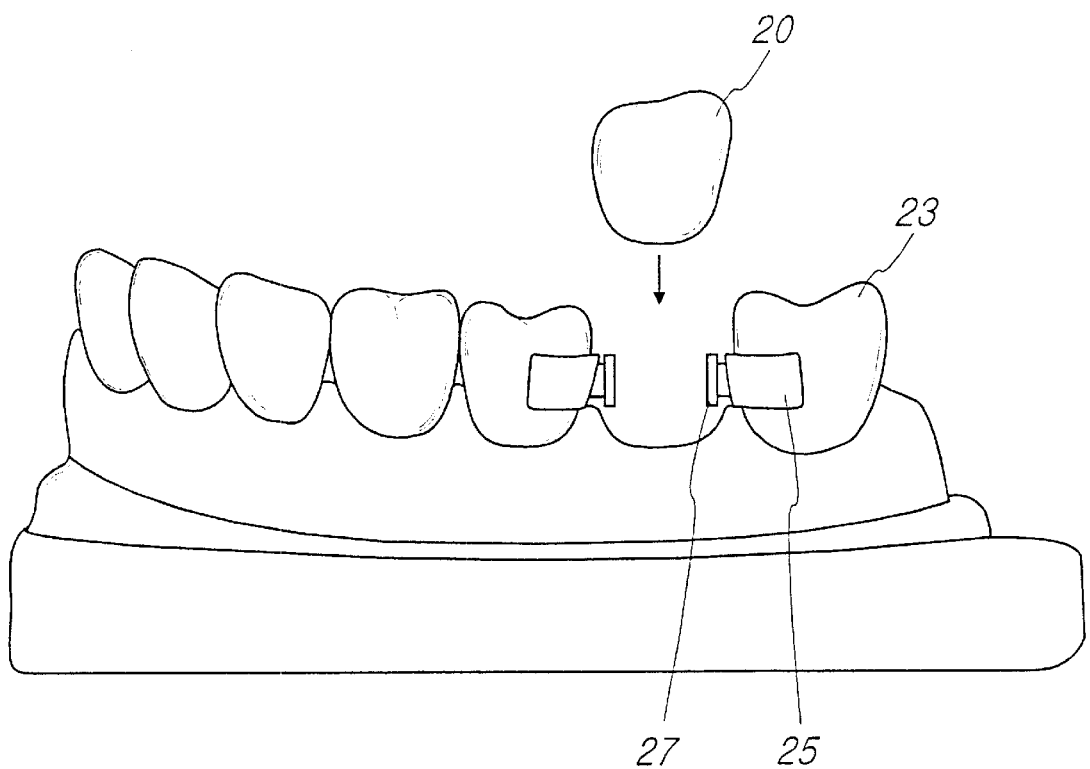
FIG. 5 is a front view illustrating a state wherein the dental prosthesis according to the present invention is about to be fitted between two adjoining teeth.
Figure 6:
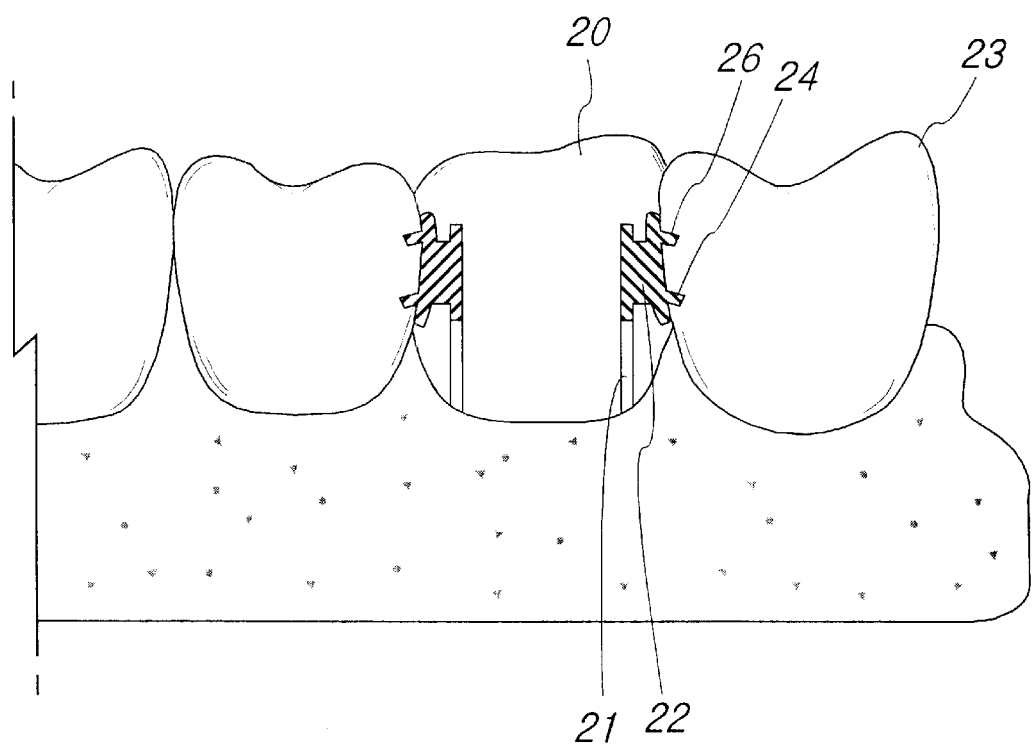
FIG. 6 is a cross-sectional view illustrating a state wherein the dental prosthesis according to the present invention is fitted between the two adjoining teeth.

FIG. 3 is an exploded perspective view illustrating an entire construction of a dental prosthesis in accordance with an embodiment of the present invention; FIG. 4 is a cross-sectional view taken along the line A—A of FIG. 3; FIG. 5 is a front view illustrating a state wherein the dental prosthesis according to the present invention is about to be fitted between two adjoining teeth; and FIG. 6 is a cross-sectional view illustrating a state wherein the dental prosthesis according to the present invention is fitted between the two adjoining teeth.

As shown in FIGS. 3 and 5, a dental prosthesis 2 according to the present invention includes an artificial tooth 20 and a pair of inlay members 22. The artificial tooth 20 serves to replace a decayed tooth and is made of a suitable material such as metal or ceramic. The artificial tooth 20 is defined, at both side walls (that is, left and right walls) thereof, with a pair of fitting grooves 21, respectively, in a manner such that the artificial tooth 20 serves as a female coupling element.

The pair of fitting grooves 21 are opened at lower ends of the side walls of the artificial tooth 20. The pair of fitting grooves 21 extend upward to a point which corresponds to about ⅔ of a height of the artificial tooth 20, in consideration of pressure resistance.

The artificial tooth 20 which is formed as described above, is independently secured using the pair of inlay members 22. The pair of inlay members 22 are respectively mounted to opposite side surfaces of two adjoining teeth 23 which are respectively located at both sides of the decayed, that is, extracted tooth, so as to secure the artificial tooth 20 to the two adjoining teeth 23.

As shown in FIG. 4, the inlay member 22 has substantially an H-shaped cross-section. Each inlay member 22 comprises a fitting part 27 and a securing part 25. The is fitting part 27 is fitted into the fitting groove 21 which is defined in the side wall of the artificial tooth 20. The securing part 25 is formed with a plurality of projections 24 in a manner such that the projections 24 obliquely extend downward to define a predetermined angle with respect to a horizontal line. The securing part 25 is secured by the medium of the projections 24 to the two adjoining teeth 23.

The pair of inlay members 22 are made of the same material as the artificial tooth 20, such as metal or ceramic, in a manner such that a dentistry receiver cannot feel heterogeneousness.

Also, as shown in FIG. 6, each adjoining tooth 23 to which the securing part 25 of each inlay member 22 is secured, is defined with a plurality of inserting grooves 26 in a manner such that the plurality of projections 24 which are formed on the securing part 25 are respectively inserted into the plurality of inserting grooves 26. The inserting grooves 26 obliquely extend downward to define the predetermined angle with respect to the horizontal line, in a manner such that pressure resistance is improved after the artificial tooth 20 is secured with respect to the two adjoining teeth 23.

In order to apply the dental prosthesis 2 according to the present invention, first, as shown in FIGS. 5 and 6, the plurality of inserting grooves 26 must be defined in the two adjoining teeth 23 before mounting the pair of inlay members 22 to the two adjoining teeth 23. In other words, the plurality of inserting grooves 26 are defined on opposite side surfaces of the two adjoining teeth 23, so that neurons of the two adjoining teeth 23 do not subject the dentistry receiver to excessive pain when inserting the projections. To this end, each inserting groove 26 is defined in such a way as to have an inner diameter of about 1–1.5 mm and a depth of about 1.5 mm.

In a state wherein the plurality of inserting grooves 26 are defined in the two adjoining teeth 23 as described above, the pair of inlay members 22 are fabricated using an impression which is taken from the mouth of the dentistry receiver, in a manner such that the securing parts 25 of the inlay members 22 can be brought into close contact with the side surfaces of the two adjoining teeth 23, respectively. Then, as the plurality of projections 24 are respectively inserted into the plurality of inserting grooves 26, a mounting operation of each inlay member 22 is completed.

At this time, the artificial tooth 20 is defined with the pair of fitting grooves 21 before the pair of inlay members 22 are secured to the two adjoining teeth 23, in a manner such that the inserting part 27 of each inlay member 22 can be fitted into the fitting groove 21. In this way, workability is improved.

If the mounting operations of the pair of inlay members 22 are completed as described above, the artificial tooth 20 is shaped using the impression which is taken from the mouth of the dentistry receiver. Thereafter, through a waxing process and a polishing process, the complete artificial tooth 20 is obtained.

In a state wherein the pair of inlay members 22 are respectively mounted to the two adjoining teeth 23 on an upper or lower jaw on which the decayed tooth exists, the artificial tooth 20 which is completed through a finishing process, is fitted on the pair of inlay members 22 from bottom to top or from top to bottom, in a manner such that the inserting parts 27 of the inlay members 22 can be closely fitted into the pair of fitting grooves 21, respectively, whereby installation of the dental prosthesis according to the present invention is completed.

As a result, the dental prosthesis according to the present invention, constructed as mentioned above, removes disadvantages which occur in the conventional crown bridge and fixed dental implant prosthesis, including damage of adjoining teeth, high cost, and various ill effects. By contrast, the dental prosthesis according to the present invention provides advantages. For example, with the present invention inferior durability in an axial direction, which is regarded as an essential problem occurring in the conventional fixed dental implant prosthesis, is overcome and pressure resistance is enhanced. In addition, the prosthetic dentistry is simplified and the cost required is reduced, whereby an economic burden on the dentistry receiver and anxiety relating to undertaking the prosthetic dentistry procedure can be relieved, resulting in a human-friendly prosthesis.

In the drawings and specification, there have been disclosed typical preferred embodiments of the invention and, although specific terms are employed, they are used in a generic and descriptive sense only and not for purposes of limitation, the scope of the invention being set forth in the following claims.

That is to say, the dental prosthesis according to the present invention is simpler and easier to use for both the dentistry provider and the dentistry receiver. Furthermore, in the present invention, various ill effects which can result after receipt of the dental prosthesis are avoided, reliability of the device is improved, and the economic burden on the dentistry receiver is remarkably lessened due to reduction in cost as compared with the prior art.

What is claimed is:

1. A dental prosthesis for a patient comprising:
    an artificial tooth adapted to fit between two adjoining teeth so as to replace a missing tooth, said artificial tooth having two side walls, each side wall having a fitting groove which is open on that side of said artificial tooth which is adapted to face the patient's gum and which extends to a point corresponding to about ⅔ of a height of said artificial tooth such that a top surface of said artificial tooth remains intact along an entirety thereof;
    a pair of inlay members for securing the artificial tooth in place, each inlay member adapted to be affixed to an adjoining tooth and serving, as a male coupling element, said artificial tooth being coupled as a female coupling element to said inlay members, each inlay member having a substantially H-shaped cross section and including,
    a securing part with a plurality of projections which extend obliquely toward the patient's gum to define an angle with respect to an essentially horizontal line corresponding to a gum line, said projections being adapted to secure said inlay member to an adjoining tooth and the angle improving pressure resistance; and
    a fitting part which extends from said securing part and is fitted into said fitting groove defined on said side wall of said artificial tooth.

2. The dental prosthesis as set forth in claim 1, wherein said fitting part includes a planar portion which is substantially parallel with said securing part and a connecting portion which joins said planar portion to said securing part, said connecting portion having a width substantially corresponding to but slightly less than a width of said fitting groove, said planar portion having a width greater than the width of said connecting portion and being inserted behind said fitting groove so that, when said dental prosthesis is mounted, said connecting portion slides within said fitting groove and said planar portion is positioned within and surrounded by said artificial tooth.

3. The dental prosthesis as set forth in claim 2, wherein said securing part is made to conform to a natural surface shape of an adjoining tooth.

4. The dental prosthesis as set forth in claim 2, wherein said projections are adapted to fit within corresponding grooves extending obliquely in an adjoining tooth.

5. The dental prosthesis as set forth in claim 1, wherein said securing part is made to conform to a natural surface shape of an adjoining tooth.

6. The dental prosthesis as set forth in claim 5, wherein a portion of said fitting part is wider than said fitting groove and substantially parallel with said securing part such that, when said dental prosthesis is mounted, said portion is positioned within and surrounded by said artificial tooth.

7. The dental prosthesis as set forth in claim 1, wherein said projections are adapted to fit within corresponding grooves extending obliquely in an adjoining tooth.

8. The dental prosthesis as set forth in claim 1, wherein a portion of a said fitting part is wider than said fitting groove and, when said dental prosthesis is mounted, is positioned within and surrounded by said artificial tooth.

9. The dental prosthesis as set forth in claim 1, wherein the fitting groove is substantially linear.

10. The dental prosthesis as set forth in claim 9, wherein said fitting part includes a planar portion which is substantially parallel with said securing part and a connecting portion which joins said planar portion to said securing part, said connecting portion having a width substantially corresponding to but slightly less than a width of said fitting groove, said planar portion having a width greater than the width of said connecting portion and being inserted behind said fitting groove so that, when said dental prosthesis is mounted, said connecting portion slides within said fitting groove and said planar portion is positioned within and surrounded by said artificial tooth.

11. The dental prosthesis as set forth in claim 10, wherein said securing part is made to conform to a natural surface shape of an adjoining tooth.

* * * * *